(12) United States Patent
DeMayo

(10) Patent No.: US 8,048,082 B1
(45) Date of Patent: Nov. 1, 2011

(54) NON-INVASIVE FEMORAL DISTRACTOR FOR USE IN KNEE SURGERY

(75) Inventor: Edward DeMayo, Greenbrae, CA (US)

(73) Assignee: Innovative Medical Product Inc., Plainville, CT (US)

( * ) Notice: Subject to any disclaimer, the term of this patent is extended or adjusted under 35 U.S.C. 154(b) by 955 days.

(21) Appl. No.: 12/001,194

(22) Filed: Dec. 11, 2007

(51) Int. Cl.
  *A61B 17/58* (2006.01)
  *A61B 17/60* (2006.01)
  *A61F 2/00* (2006.01)
(52) U.S. Cl. .......................................................... 606/90
(58) Field of Classification Search .................. 600/227, 600/228; 606/90; 222/326
  See application file for complete search history.

(56) References Cited

U.S. PATENT DOCUMENTS

| 4,072,254 | A | * | 2/1978 | Cox | 222/391 |
| 5,180,131 | A | * | 1/1993 | Few | 248/352 |
| 5,704,900 | A | * | 1/1998 | Dobrovolny et al. | 600/229 |
| 7,003,827 | B2 | * | 2/2006 | DeMayo | 5/600 |
| 7,763,027 | B2 | * | 7/2010 | Irving | 606/88 |
| 2008/0228191 | A1 | * | 9/2008 | Downs et al. | 606/90 |

* cited by examiner

*Primary Examiner* — Thomas C. Barrett
*Assistant Examiner* — Christine Nelson

(57) ABSTRACT

A femoral distractor includes a top post for positioning under a patient's knee and a bottom pin for fixed attachment to a hospital bed rail. A vertical rod extends between the top post and horizontal bottom pin to move the knee joint in the vertical direction upon operation of a trigger assembly.

4 Claims, 2 Drawing Sheets

NON-INVASIVE FEMORAL DISTRACTOR FOR USE IN KNEE SURGERY

BACKGROUND OF THE INVENTION

Devices such as described within U.S. Pat. No. 5,116,338 entitled "Apparatus for Knee Prosthesis" and U.S. Pat. No. 5,308,350 entitled "Femoral Distractor for Use in Knee Surgery" are currently available for assisting a surgeon in knee surgery by employing means for insertion within the knee joint to retract or distract the femur from the tibia.

The use of such sterile pins, rods, or sterile spreaders and the like to provide insertion requires considerable time and effort to insure insertion in a precise and antiseptic manner within the joint space and thereby create enough space for instruments and implantable devices.

It would be highly advantageous to be able retract or distract the femur from the tibia during such knee surgery without having to insert any pins, rods, or sterile spreaders into the joint space thereby obscuring vision and occupying instrument space.

On purpose of the instant invention is to describe a simple and effective approach to femur distraction during knee surgery that is performed external to the knee joint, per se, for increasing surgical vision and surgical space when preparing to implant a prosthetic device.

SUMMARY OF THE INVENTION

A femoral distractor includes a top post at one end for positioning under a patient's knee when the knee has been incised to expose the femur and tibia and a bottom pin at the opposite end for fixed attachment to a hospital bed rail or a knee positioner unit. A vertical rod extends between the top post and horizontal bottom pin for controlled movement of the top post to move the knee joint in the vertical direction upon operation of a hand-operated and spring-loaded trigger assembly.

DESCRIPTION OF THE PREFERRED EMBODIMENT

Figure 1:
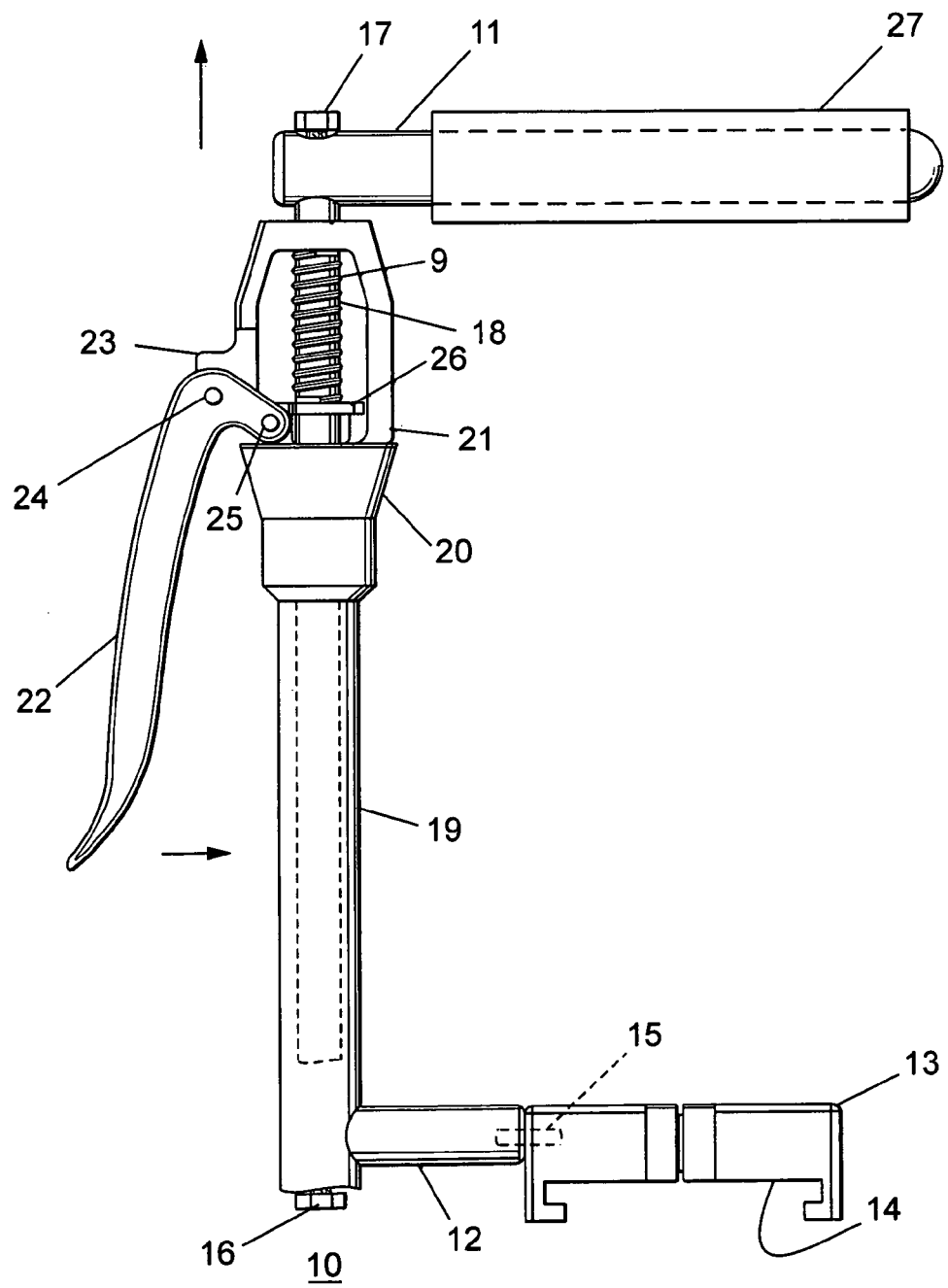
FIG. 1 is a side view of the femoral distractor unit in accordance with the invention.

As shown in FIG. 1, the femoral distractor unit 10 includes a knee support bar 11 at one end for supporting a patient's knee during surgery and a base support bar 12 at the opposite end for attaching to a support base 13, similar to that described within U.S. Pat. No. 7,003,827 entitled "Operating Table Support Clamp", which patent is incorporated herein for purposes of reference.

An outer cylinder 19 interconnects between the support bar 11 and support base 13 via the support bar 12 at one end and the U-shaped support 21 at the opposite end thereof. The support bar 12 is attached to the support base 13 via connector pin 15 in press-fit relation to allow the unit 10 to move along the knee positioner carriage rail (not shown) via the extended slot 14.

Although the unit 10 is arranged herein for attachment to the knee positioner, device, per se, as described in the aforementioned U.S. Pat. No. 7,003,827, for example, it is to be understood that the unit could be directly attached to an operating table side rail, via a modified clamp (not shown.)

The driver rod 18 extends within the outer cylinder 19 and is attached to the support bar 11, via screw 17 to move the support bar 11 in the indicated vertical direction against the bias of the compression spring 9 arranged within the U-shaped support 21. A sterile foam cylinder 27 is arranged on the support bar 11 to insure sterile contact with the patient's knee (not shown).

The lever 26, arranged on the driver rod 18 in press-fit relation, extends, at one end, under the lever pin 25.

The handle lever 22 is pivotally attached to the flange 23 extending from the U-shaped support 21 via pivot pin 24. When the handle lever 22 is moved toward the outer cylinder 19, lever pin 25 drives the spring lever 26 and the attached driver rod 18 in the vertical direction against the bias of the compression spring 9 to thereby move the attached support bar 11 in the vertical direction. The relative movement of the handle lever 22 towards the outer cylinder 19 governs the associated movement of the driver rod and attached support bar 11 in a controlled manner.

Maintaining the handle lever 22 in a determined position relative to the outer cylinder 19 holds the support bar in an associated determined position, during knee surgery, which is an important feature of the instant invention.

When the patient's knee (not shown) is arranged over the support bar 11 and the knee is incised to separate the femur and tibia, movement of the handle lever 22 controls the position of the knee and accordingly determines the precise distance that the femur is separated from the tibia, during the course of the knee surgery.

To move the femur toward the tibia, tension on the handle lever 22 is controllably released to allow the compression spring 9 to force the driver rod 18 and attached support bar 11 to thereby move the femur in the opposite vertical direction.

Figure 2:
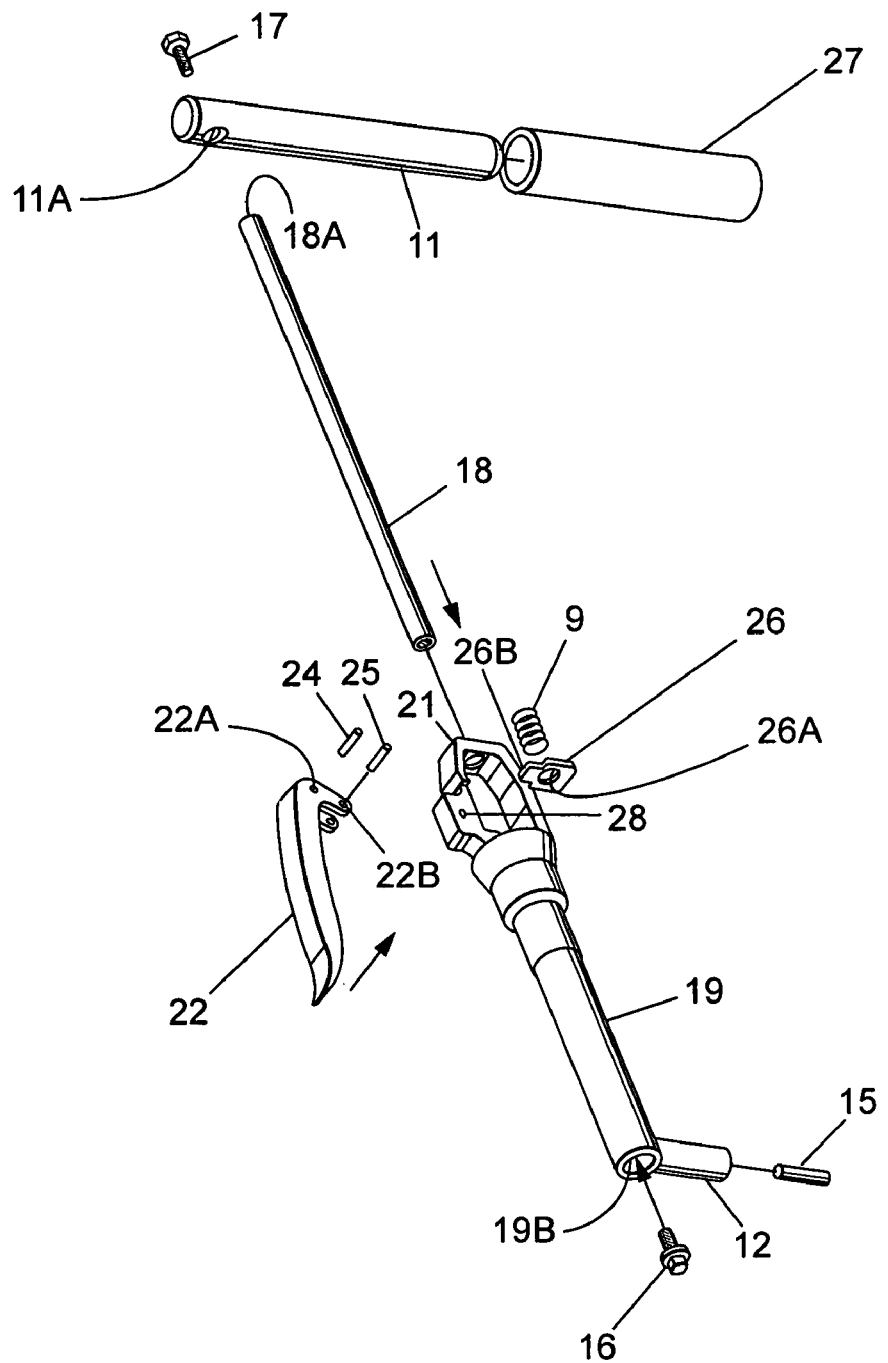
FIG. 2 is a front perspective view of the components of the femoral distractor of FIG. 1 prior to assembly.

The arrangement of the components within the femoral distractor unit 10 is best seen by now referring to FIG. 2.

The outer cylinder 19 having the support bar 12 welded at the end, receives the connector pin 15 for attachment to a knee positioner, as described earlier, along with a threaded opening 19B for allowing the attachment of the outer cylinder 19 to a surgical knee positioner unit (not shown) via threaded bolt 16.

The U-shaped support 21 is welded at the opposite end of the outer cylinder 19 and receives the driver spring 9 and release spring lever 26, which includes an opening 26A for receiving the driver rod 18 in press-fit relation.

The handle lever 22 includes apertures 22A, for attachment to the U-shaped support 21 via aperture 28 and pivot pin 24 along with apertures 22B for receiving lever pin 25 that is positioned under one end 26B of the spring lever 26 for the purposes described earlier with reference to FIG. 1.

The driver rod 18 extends thru aperture 11A, at one end of the support bar 11, for attachment to the support bar via screw 17. Prior to surgery, the sterile foam cylinder 27 is positioned over the support bar 11 to provide sterile contact with the patient's knee (not shown).

A simple and efficient arrangement has been described herein whereby a patient's femur can be precisely separated from the tibia during knee surgery without requiring insertions of pins, rods, spreaders and the like into the femur/tibia space or medullar canal as often required with prior knee surgery operations.

What is claimed is:

1. A surgical distractor unit for separating a pair of adjacent bones within a patient's joint during surgery without insertion within said patient comprising:
   an outer cylinder arranged between a patient's support bar at one end and a unit support bar for said distractor unit at an opposite end thereof, said patient's support bar arranged for positioning in abutment with a patient's joint;
   a driver rod within said outer cylinder arranged for moving said patient's support bar relative to said distractor unit support bar to thereby control separation distance between said patients bones before, during and after surgery thereon;
   a U-shaped support attached to said outer cylinder proximate said patient's support bar and having a handle lever pivotally attached to one part thereof; and
   a compression spring arranged within said U-shaped support about said driver rod for controlled movement of said driver rod relative to said outer cylinder.

2. The surgical distractor unit of claim 1 wherein said unit support bar includes means for attachment to an operating table side rail or a patient limb support device.

3. The surgical distractor unit of claim 1 including a spring lever within said U-shaped support, said spring lever being fixedly attached to a second part of said handle lever proximate said one part, said driver rod passing thru an opening within said spring lever in press-fit relation whereby movement of said handle lever in a first horizontal direction in a horizontal plane drives said spring lever and said driver rod in a first vertical direction in a vertical plane.

4. The surgical distractor unit of claim 3 wherein said compression spring is arranged intermediate a top part of said U-shaped support and said spring lever whereby movement of said handle lever in a horizontal second direction in said horizontal plane returns said spring lever and said driver rod in a vertical second direction in said vertical plane opposite said first vertical direction in said vertical plane.

* * * * *